(12) United States Patent
Pastrello et al.

(10) Patent No.: US 8,790,232 B2
(45) Date of Patent: Jul. 29, 2014

(54) MACHINE FOR MAKING ABSORBENT ITEMS

(75) Inventors: Gabriele Pastrello, Milan (IT); Luca Pedretti, Crema (IT); Alberto Perego, Milan (IT); Matteo Piantoni, Albino (IT)

(73) Assignee: GDM S.p.A. (IT)

( * ) Notice: Subject to any disclaimer, the term of this patent is extended or adjusted under 35 U.S.C. 154(b) by 866 days.

(21) Appl. No.: 13/001,140

(22) PCT Filed: Jul. 3, 2009
(Under 37 CFR 1.47)

(86) PCT No.: PCT/IB2009/052910
§ 371 (c)(1),
(2), (4) Date: Aug. 1, 2011

(87) PCT Pub. No.: WO2010/001361
PCT Pub. Date: Jan. 7, 2010

(65) Prior Publication Data
US 2012/0190523 A1   Jul. 26, 2012

(30) Foreign Application Priority Data

Jul. 4, 2008   (IT) .............................. BO2008A0426

(51) Int. Cl.
*B65H 39/14* (2006.01)

(52) U.S. Cl.
USPC ......................................... 493/379; 493/381

(58) Field of Classification Search
USPC .......................................... 493/374, 379–382
IPC ............................................ B65H 39/14,39/16
See application file for complete search history.

(56) References Cited

U.S. PATENT DOCUMENTS 4,578,133 A * 3/1986 Oshefsky et al. ............. 156/164
5,224,405 A * 7/1993 Pohjola .............................. 83/24

(Continued)

FOREIGN PATENT DOCUMENTS

| EP | 1132325 | 9/2001 |
|---|---|---|
| WO | 98/00356 | 1/1998 |
| WO | 2008/155618 | 12/2008 |

OTHER PUBLICATIONS

International Search Report and Written Opinion dated Nov. 5, 2009 from corresponding application.

*Primary Examiner* — Christopher Harmon
(74) *Attorney, Agent, or Firm* — Timothy J. Klima; Shuttleworth & Ingersoll, PLC

(57) ABSTRACT

A machine for making absorbent items comprises a conveyor (9) for feeding a continuous strip (7) of absorbent items in a predetermined direction L, a cutting element (11) for cutting the strip into single absorbent items (2), a unit for feeding and applying to each stretch of the strip which will constitute a single absorbent item (2) a pair of fastening and closure elements (6) for the items; the unit (13) comprising a roller (18) for conveying a succession of pieces (15), intended to form the fastening elements (6), a separating device (22) consisting of a pair of rollers (20, 21) which are at a tangent to the conveyor roller (18) and equipped with suction seats (29, 30), able to slide parallel with their axes, for forming respective successions (32, 33) of pieces (15), which are spaced out in a direction T transversal to the direction L, by a stretch having a predetermined length, a roller (23) for forming pairs of pieces (15), which is at a tangent to both of the rollers (20, 21) and equipped with a first and a second ring of seats, each seat (34) of the first ring being axially aligned with a seat (35) of the second ring so as to form a succession of pairs of pieces (15) which are aligned according to the direction T; an accelerator roller (25) which is at a tangent to the roller (23) and to the feed conveyor (9) varies the pitch P of the pairs of pieces (15) according to the pitch P1 of the stretches of strip (7) intended to form the single absorbent items (2).

5 Claims, 3 Drawing Sheets

(56) References Cited

U.S. PATENT DOCUMENTS

| | | | |
|---|---|---|---|
| 6,481,362 B2 * | 11/2002 | Hietpas et al. | 112/475.06 |
| 6,736,923 B1 * | 5/2004 | Franzmann et al. | 156/265 |
| 6,942,086 B2 * | 9/2005 | Bridges et al. | 198/377.08 |
| 8,172,977 B2 * | 5/2012 | McCabe et al. | 156/265 |
| 2003/0051802 A1 | 3/2003 | Hargett et al. | |
| 2008/0099124 A1 * | 5/2008 | Bianco | 156/66 |
| 2008/0276439 A1 * | 11/2008 | Andrews et al. | 29/428 |
| 2010/0192739 A1 * | 8/2010 | Piantoni et al. | 83/26 |

\* cited by examiner

MACHINE FOR MAKING ABSORBENT ITEMS

This application is the National Phase of International Application PCT/IB2009/052910 filed Jul. 3, 2009 which designated the U.S. and that International Application was published under PCT Article 21(2) in English.

This application claims priority to Italian Patent Application No. BO2008A000426 filed Jul. 4, 2008 and PCT Application No, PCT/IB2009/052910 filed Jul. 3, 2009, which applications are incorporated by reference herein.

TECHNICAL FIELD

The present invention relates to a machine for making absorbent items.

In particular, the present invention is used in the production of disposable nappies for babies or incontinence pads for adults, to which this text explicitly refers.

BACKGROUND ART

As is known, nappies or incontinence pads comprise an absorbent pad, usually made of cellulose fibres enclosed in a soft outer element, consisting on one side of a permeable sheet of "non-woven fabric", and on the other side of an impermeable sheet of polyethylene. The two sheets are joined to each other along the respective edges, which are suitably shaped and equipped with retaining elastic elements.

In prior art machines the single nappies or incontinence pads are obtained by means of an operation for cutting into pieces a continuous strip of nappies or incontinence pads which are adjacent to each other and still joined one after another.

Relative to their longitudinal axis, the nappies or incontinence pads comprise a front portion and a rear portion, where two fastening and closure elements are usually fixed, said elements designed to guarantee correct and stable positioning of the item around the user's hips.

The fastening and closure elements are generally fed in pairs and applied on the continuous strip of nappies or incontinence pads before the strip is divided into single nappies or incontinence pads.

Patent application BO2007A000431 by the same Applicant describes a machine for making absorbent items of the above-mentioned type.

Said machine comprises a conveyor for feeding the continuous strip of absorbent items to the device for cutting it into the single absorbent items, through a fastening and closure element feed station.

Said elements are formed, arranged in pairs and applied by a unit whose infeed is fed with a continuous web of elastomeric material.

Said unit comprises a cutting element comprising a pair of rollers rotating in opposite directions which are substantially at a tangent to each other, being designed to obtain from the continuous web a succession of pieces, forming trapezoidal fastening elements, by means of a succession of cuts alternating obliquely in opposite directions along the longitudinal axis of the web.

After that operation the web is separated into a continuous succession of pieces which have a trapezoidal shape, with reference to their bases alternately rotated through 180° relative to each other.

Downstream of the cutting element there is a separating roller which spaces out the pieces. For that purpose, the separating roller, substantially at a tangent to a roller of the above-mentioned pair of cutting roller, has a prismatic shape and each of its faces, at an angle to the adjacent faces, is equipped with a suction seat that is substantially rectangular and designed to receive and retain one of the pieces.

Each suction seat can also move with a reciprocating motion parallel with the axis of the separating roller during the latter's rotation and in the opposite direction to the adjacent seats, between the position for receiving a piece and a second position, reached at a position in which it is at a tangent to a roller for forming pairs of fastening elements.

During the transfer between the separating roller infeed and outfeed, the fastening elements consequently pass from the condition in which they are aligned in a single row to a condition in which they are aligned in two rows which are offset relative to each other and consist of trapezoidal pieces arranged so that the larger bases of the pieces of one row are opposite the larger bases of the pieces of the other row.

Finally, the feed unit comprises the above-mentioned roller for forming pairs of fastening elements, which aligns transversally to their direction of feed each fastening element in one row with an adjacent fastening element in the second row.

For that purpose, the pair forming roller comprises two drums which are coaxial, each having a plurality of radial arms separated from each other by equal angles for using respective suction seats to pick up the fastening elements from the separating roller. During the transfer from the station for pick up from the separating roller to the continuous strip feed line, two radial arms relative to two successive pieces which are part of each of the rows perform a relative movement, thus forming a pair aligned transversally to the direction of feed.

The trapezoidal fastening elements are then applied in pairs at their larger bases and according to a predetermined pitch, to the continuous strip of absorbent items.

However, the fastening element feed unit of the type described limits the operating speed of the machine to which it belongs.

This is firstly due to the extreme mechanical complexity of the roller for forming the pairs of fastening elements.

Secondly, in particular at high operating speeds, during relative sliding, transversal to their direction of feed, of the seats of the separating roller, despite its prismatic shape, there may be interference between the edges of the trapezoidal pieces, with the risk that they may become detached from the respective supports.

DISCLOSURE OF THE INVENTION

The present invention has for an aim to provide a method and a machine for making absorbent items which are free of the disadvantages listed above with reference to the prior art.

The present invention provides a method and a machine for making absorbent items as described in one or more of the appended claims.

BRIEF DESCRIPTION OF THE DRAWINGS

The present invention is described below with reference to the accompanying drawings, which illustrate a preferred, non-limiting embodiment, in which.

DETAILED DESCRIPTION OF THE PREFERRED EMBODIMENTS OF THE INVENTION

Figure 1:
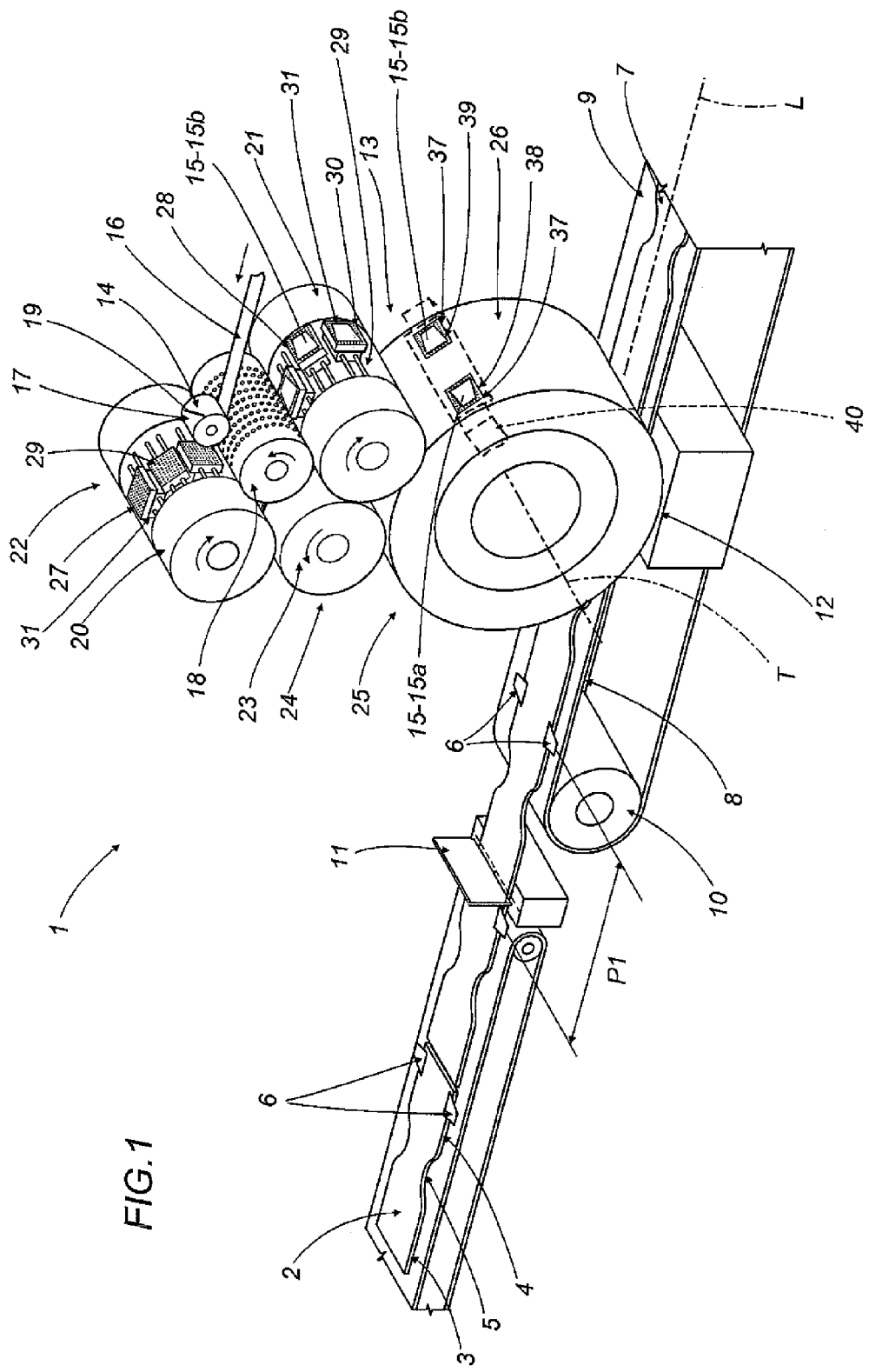
FIG. 1 is a schematic perspective view of a machine for making absorbent items according to the present invention.
Figure 2:
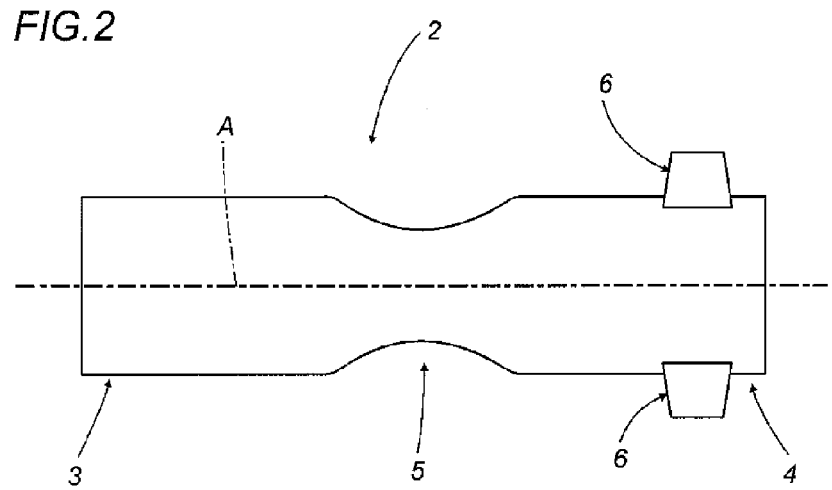
FIG. 2 is a plan view of an absorbent item made by the machine of FIG. 1.

With reference to FIGS. 1 and 2, the numeral 1 denotes as a whole a machine for making absorbent items 2, in particular disposable nappies or incontinence pads which have a substantially rectangular shape and which, with reference to the longitudinal axis A, comprise a first or front part 3 and a second or rear part 4, separated from each other by a central part 5 located between inwardly curving stretches of the two longitudinal sides of the item 2.

The items 2 comprise an inner absorbent pad, usually made of cellulose fibres enclosed in a soft outer element and formed on one side by a permeable sheet of "non-woven fabric" and on the other side by an impermeable sheet of polyethylene.

Along its waistband line each item 2 is also equipped with two fastening and closure elements 6, or tabs, projecting from the sides of the body of the item 2. More precisely, the elements 6 project from the rear part 4 of the item 2 and are designed, in practice, to be superposed on respective lateral zones of the front part 3, for fastening the item 2 around the user's hips.

The elements 6 usually comprise pieces in sheet form, preferably of elastic material and have a surface partly covered with an adhesive substance, or equipped with other rapid fastening means.

The machine 1 comprises a line 8 for feeding, in a predetermined direction L, a continuous strip 7 of items 2 which are arranged one after another.

The feed line 8 extends horizontally along a conveyor 9 comprising a belt looped around end rollers 10 (only one of which is illustrated), as far as a cutting station where a cutting element 11 separates the continuous strip 7 into the single items 2.

Along the conveyor 9, upstream of the cutting element 11, there is a station 12 for feeding the fastening elements 6 using a unit 13 comprising a plurality of rotary conveyors consisting of rollers with horizontal axes parallel with a direction T transversal to the direction L.

Figure 3:
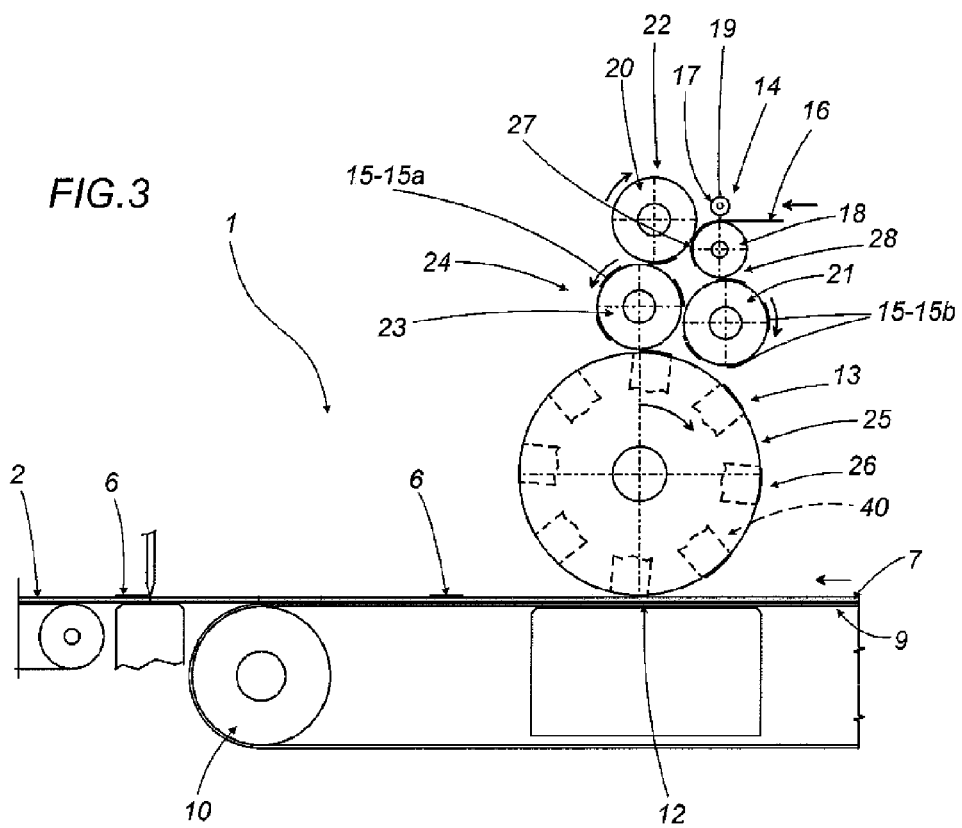
FIG. 3 is a schematic front view of a detail of FIG. 1.
Figure 4A:
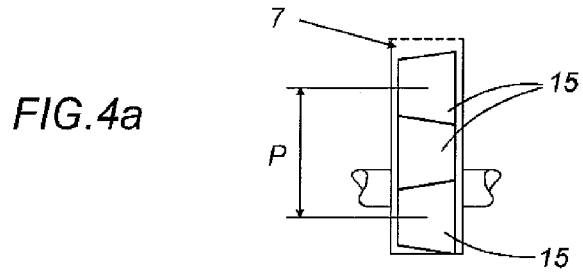
FIGS. 4a, 4b, 4c, 4d, 4e are schematic views of several operating steps of the machine of FIG. 1.
Figure 4B:
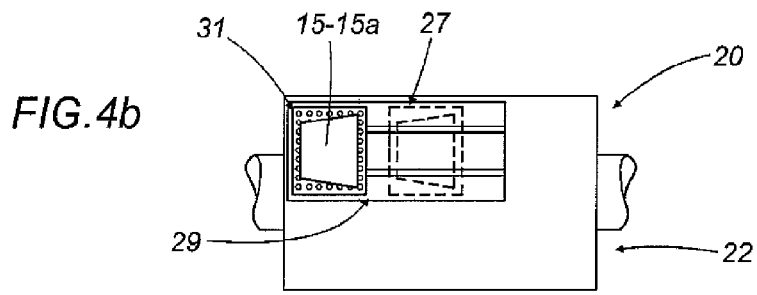
Figure 4C:
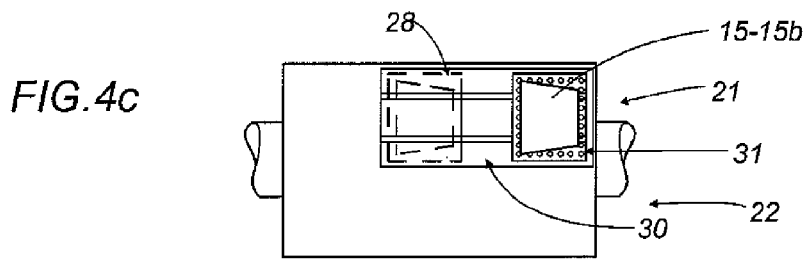
Figure 4D:
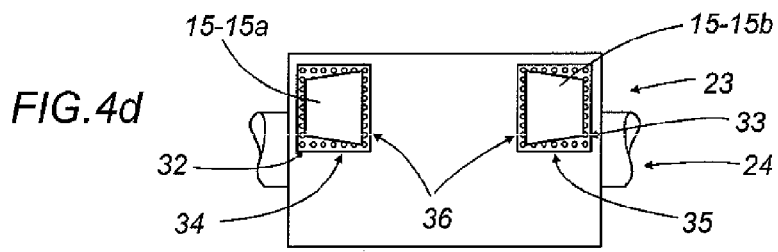
Figure 4E:
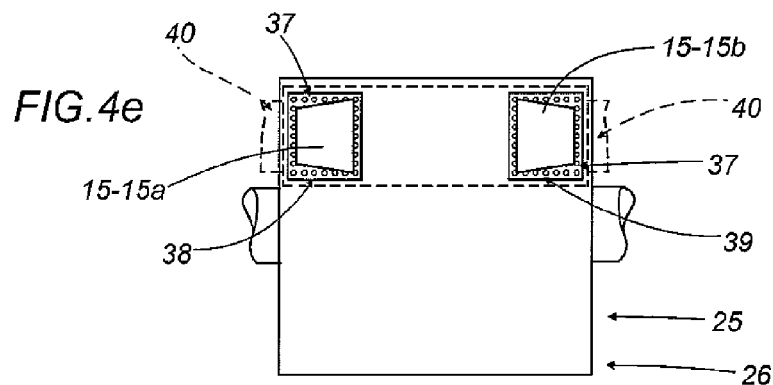

With reference also to FIGS. 3 and 4, the unit 13 comprises, at its upper end, a device 14 for cutting pieces 15 which are intended to form the fastening elements 6, fed with a continuous web 16 of elastomeric material unwound from a reel, not illustrated.

The cutting device 14 comprises two rollers rotating in opposite directions and operating in conjunction with each other. More precisely, it comprises an upper, cutting roller 17, rotating in a clockwise direction, and a lower roller 18, rotating in an anti-clockwise direction, designed to convey the pieces 15.

The roller 17 has two diametrically opposed blades 19 arranged obliquely, relative to the roller axis, in opposite directions to each other.

The conveyor roller 18 has a cylindrical surface with holes in it which are connected to a suction source, for retaining the pieces 15 after they have been separated from the web 16.

Substantially at a tangent to the conveyor roller 18, from upstream to downstream with reference to its direction of rotation, there are two rollers 20 and 21, both rotating in a clockwise direction, forming a separator device 22 for forming respective successions of fastening elements 6.

The rollers 20 and 21 are in turn substantially at a tangent to a roller 23 rotating in an anti-clockwise direction and forming a device 24 for forming pairs of pieces 15.

Finally, the numeral 25 denotes a roller, rotating in a clockwise direction, which is substantially at a tangent to both the roller 23 and the conveyor 9 and forming an accelerator device 26.

With reference also to FIGS. 4a, 4b, 4c, 4d, 4e, during its passage between the roller 17, equipped with oblique blades 19, and the roller 18, the web 16 is divided into pieces 15 having a trapezoidal shape which, retained by suction on the cylindrical surface of the roller 18, are alternated and angled in opposite directions to each other.

For greater clarity in the accompanying drawings the pieces with the larger base towards the right are labelled 15a and the pieces with the larger base towards the left are labelled 15b.

The roller 20 and the roller 21, at tangents to the roller 18 at two transfer positions respectively labelled 27 and 28, are substantially equal, rotate in a clockwise direction and have on their respective cylindrical surfaces a plurality of seats 29 and 30 separated from each other by equal angles according to a predetermined pitch P.

Each seat 29, 30, designed to receive and retain by suction one of the trapezoidal pieces 15, comprises a block 31 able to slide in a direction parallel with the axes of the rollers, controlled by actuator means not illustrated, between two limit positions.

More precisely, the blocks 31 relative to the roller 20 pick up, at the position 27, the pieces 15a with the larger base towards the right, whilst the blocks 31 relative to the roller 21 pick up, at the position 28, the pieces 15b with the larger base towards the left.

Starting from the respective transfer positions 27 and 28, the blocks 31 slide in opposite directions to each other during rotation of the rollers 20 and 21, forming respective successions 32 and 33, each comprising pieces angled in the same way and spaced out, parallel with the axes of the rollers, by a distance whose length is less than the transversal dimensions of the strip 7.

The pair forming roller 23, rotating in an anti-clockwise direction, has on its outer cylindrical surface close to each of the two longitudinal ends a ring of seats, respectively labelled 34 and 35 from left to right, separated from each other by equal angles according to the pitch P and arranged so that each seat 34 is axially aligned with a seat 35, forming a pair labelled 36 with it.

During its rotation the roller 23 receives, relative to each pair 36 of seats 34, 35, first a piece 15a from the roller 20 and then a piece 15b from the roller 21, forming a pair of pieces 15 separated by the above-mentioned distance whose length is less than the transversal dimensions of the strip 7.

Downstream of the position where the roller 23 and the roller 21 are at a tangent to each other, the pair of pieces 15 is transferred from the pair 36 of seats 34, 35 to a corresponding pair 37 of suction seats 38, 39 on the accelerator roller 25.

Each pair 37 of seats 38, 39 is mounted on a radial rod 40, able to oscillate, during rotation of the roller 25, on an axis parallel with the direction T, controlled by cam actuator means (not illustrated) of the known type and described in the above-mentioned patent application BO2007A000431.

Consequently, at the pick-up position for a pair of pieces 15 the respective suction seats 38, 39 of the roller 25 have the tangential velocity of the roller 23, whilst at the moment of transfer of the pieces 15 the tangential velocity of the suction seats 37 coincides with the strip 7 feed speed, with consequent passage of the pitch of the pairs of pieces 15 from the above-mentioned value P to a value P1, coinciding with the pitch of the stretches of the strip 7 intended to form the single nappies or incontinence pads.

At the position where the roller 25 and the conveyor 9 are at a tangent to each other, the fastening elements 6 are applied to each of said stretches of the strip 7.

In other words, the machine 1 described above allows items 2 to be made according to a method in which the fastening and closure elements are obtained by cutting the continuous web 16 without waste to obtain from the web 16 a first set and a second set of fastening and closure elements in which the elements from the first set are angled in the opposite direction to and are alternated with the elements from the second set. Then the cut web 16 is fed through the station 27, in which the elements from the first set are picked up, and through the station 28, in which the elements from the second set are picked up. The elements from the first set are then fed by the roller 20 along a first path starting from the station 27, whilst the elements from the second set are fed by the roller 21 along a second path, separate from the first, starting from the station 28. As they are fed along the first path, the elements from the first set are moved sideways in a first direction. Simultaneously, as they are fed along the second path, the elements from the second set are moved sideways in a second direction which is opposite to the first direction. Both of the movements are in a direction parallel with the axes of the rollers 20 and 21.

Then the elements from the first set and the second set are transferred separately from the rollers 20 and 21 to the roller 23, which forms a shared third feed path for the fastening elements. On the roller 23, alongside each element from the first set, a corresponding element from the second set is placed in a synchronised fashion, spaced out from and angled in the opposite direction to the element from the first set. Moreover, on the drum 23, after placing the elements alongside each other, in each pair of elements positioned side by side, the element from the first set and the element from the second set are further spaced out until the reciprocal distance established along the waistband line is reached.

From the above description it is apparent how dividing the pieces 15 between the two rollers 20 and 21 according to their orientation and the subsequent formation of the pairs on the roller 23 allows a significant mechanical simplification compared with prior art solutions and eliminates the above-mentioned disadvantage relating to interference between the edges of the trapezoidal pieces, with the risk that they will become detached from the respective supports, during their transfer.

The invention claimed is:

1. A method for making absorbent items, where each item is equipped, along the waistband line, with at least one pair of fastening and closure elements, or tabs, projecting from the sides of the body of the item, the fastening and closure elements being obtained by cutting a continuous web without waste so as to obtain a first set and a second set of said elements from the web, where the elements from the first set are angled in the opposite direction to and are alternated with the elements from the second set; each pair of fastening and closure elements consisting of one element from the first set and one element from the second set; the method comprising:

feeding the cut web through a first pick-up station, in which the elements from the first set are picked up, and then through a second pick-up station, in which the elements from the second set are picked up;

feeding the elements from the first set along a first path starting from the first station;

feeding the elements from the second set along a second path, separate from the first, starting from the second station;

moving the elements from the first set sideways in a first direction as they are fed along the first path;

moving the elements from the second set sideways in a second direction which is opposite to the first direction as they are fed along the second path;

bringing together the elements from the first and second sets, transferring them separately to a shared third path along which each element from the first set is placed alongside, in a synchronised fashion, spaced out from and angled in the opposite direction to a corresponding element from the second set.

2. The method according to claim 1, wherein, along the third path, in each pair of elements set alongside each other, the element from the first set and the element from the second set are further spaced out until they are separated by a predetermined distance along the waistband line.

3. A machine for making absorbent items, comprising a conveyor for feeding a continuous strip of absorbent item material in a predetermined direction (L), a cutting element for cutting the strip into single absorbent items, a unit for feeding and applying to stretches of the strip, which will constitute single absorbent items, at least one pair of fastening and closure elements for the items, said unit comprising a device for cutting a continuous web into pieces forming the fastening and closure elements and for conveying a succession of said pieces, wherein the unit consists of a plurality of conveyors rotating around axes parallel with a direction (T) which is transversal to the direction (L), comprising a roller for conveying the succession of pieces, a separating device consisting of a pair of rollers which are substantially at a tangent to the conveyor roller at a first and a second transfer position and equipped with suction seats, reciprocatingly movable parallel with the direction (T), for forming respective successions of pieces which are spaced along the direction (T) by a stretch having a predetermined length, a roller for forming pairs of pieces, which is at a tangent to both of the rollers at a third and a fourth transfer position and equipped with a first and a second ring of seats, each seat of the first ring being axially aligned with a seat of the second ring so as to form a succession of pairs of pieces which are aligned according to the direction (T).

4. The machine for making absorbent items according to claim 3, wherein the unit comprises another rotating conveyor at a tangent to the roller and to the feed conveyor, the additional conveyor consisting of an accelerator roller for varying the pitch of the pairs of pieces and for applying the pair to the strip.

5. The machine for making absorbent items according to claim 4, wherein the succession of pieces fed by the conveyor roller have a trapezoidal shape and are alternated, retained by suction by the roller, being angled in opposite directions to each other, the rollers each being designed to pick up from the conveyor roller pieces which are angled in the same direction and to use them to form respective successions which are spaced according to the direction (T), by a distance that is approximately the transversal dimension of the strip.

* * * * *